(12) United States Patent
Rock et al.

(10) Patent No.: US 7,202,443 B2
(45) Date of Patent: Apr. 10, 2007

(54) ELECTRIC HEATING/WARMING FABRIC ARTICLES

(75) Inventors: Moshe Rock, Brookline, MA (US); Vikram Sharma, Stoneham, MA (US)

(73) Assignee: Malden Mills Industries, Inc., Lawrence, MA (US)

( * ) Notice: Subject to any disclaimer, the term of this patent is extended or adjusted under 35 U.S.C. 154(b) by 0 days.

(21) Appl. No.: 10/927,665

(22) Filed: Aug. 27, 2004

(65) Prior Publication Data

US 2005/0127057 A1 Jun. 16, 2005

Related U.S. Application Data

(63) Continuation-in-part of application No. 10/339,083, filed on Jan. 9, 2003.

(60) Provisional application No. 60/386,180, filed on Jan. 14, 2002, now abandoned.

(51) Int. Cl.
*H05B 1/00* (2006.01)

(52) U.S. Cl. ............... 219/211; 219/212; 219/528; 219/529; 219/549; 2/159; 2/905; 2/906; 338/210; 338/306; 338/311

(58) Field of Classification Search ............... 219/211, 219/212, 528, 529, 549; 338/208, 210, 211, 338/306–309; 2/905, 906, 159, 167, 458
See application file for complete search history.

(56) References Cited

U.S. PATENT DOCUMENTS

| | | | |
|---|---|---|---|
| 2,713,193 A | 7/1955 | Robbins et al. | |
| 3,513,297 A | 5/1970 | Jordan | |
| 3,539,767 A | 11/1970 | Eisler | |
| 3,697,728 A | 10/1972 | Stirzenbecher | |
| 3,729,613 A | 4/1973 | Deloire et al. | |
| 3,869,596 A | 3/1975 | Howie | |
| 3,978,183 A | 8/1976 | Erickson | |
| 4,021,640 A | 5/1977 | Gross et al. | |
| 4,044,221 A | 8/1977 | Kuhn | |
| 4,061,898 A * | 12/1977 | Murray et al. | 219/211 |
| 4,065,660 A | 12/1977 | Berard | |
| 4,147,921 A * | 4/1979 | Walter et al. | 219/211 |
| 4,245,149 A | 1/1981 | Fairlie | |
| 4,272,673 A | 6/1981 | Semanaz et al. | |
| 4,320,286 A | 3/1982 | Borrup | |
| 4,485,297 A | 11/1984 | Grise et al. | |
| 4,590,359 A | 5/1986 | Mobius | |
| 4,656,339 A | 4/1987 | Grise | |

(Continued)

FOREIGN PATENT DOCUMENTS

DE 33 34 744 4/1984

(Continued)

*Primary Examiner*—Robin Evans
*Assistant Examiner*—Leonid Fastovsky
(74) *Attorney, Agent, or Firm*—Fish & Richardson P.C.

(57) ABSTRACT

Electric heating/warming composite fabric articles have at least a fabric layer having inner and outer surfaces, and an electric heating/warming element, formed, e.g., of die cut, metallized textile or plastic sheeting or metal foil, affixed at the inner surface of the fabric layer and adapted to generate heating/warming when connected to a power source. A barrier layer may be positioned, for example, adjacent to the inner surface of the fabric layer; e.g., with the electric heating/warming element formed thereupon, including to protect the electric circuit, e.g. against abrasion.

24 Claims, 12 Drawing Sheets

U.S. PATENT DOCUMENTS

| | | |
|---|---|---|
| 4,713,531 A | 12/1987 | Fennekels et al. |
| 4,736,088 A | 4/1988 | Bart |
| 4,764,665 A | 8/1988 | Orban et al. |
| 4,774,397 A | 9/1988 | Grise |
| 4,814,586 A | 3/1989 | Grise |
| 4,849,225 A | 7/1989 | Grise et al. |
| 4,857,384 A | 8/1989 | Mio et al. |
| 4,888,089 A | 12/1989 | Marstiller et al. |
| 4,892,998 A | 1/1990 | Marstiller et al. |
| 4,912,306 A | 3/1990 | Grise et al. |
| 4,950,868 A | 8/1990 | Moss et al. |
| 4,983,814 A | 1/1991 | Ohgushi et al. |
| 5,019,797 A | 5/1991 | Marstiller et al. |
| 5,081,339 A | 1/1992 | Stine |
| 5,151,578 A | 9/1992 | Phillips |
| 5,298,722 A | 3/1994 | Tanaka |
| 5,364,678 A | 11/1994 | Lumb et al. |
| 5,432,322 A | 7/1995 | Ingram et al. |
| 5,484,983 A | 1/1996 | Roell |
| 5,547,733 A | 8/1996 | Rock et al. |
| 5,679,377 A | 10/1997 | Niibe et al. |
| 5,804,798 A | 9/1998 | Takeda |
| 5,824,996 A | 10/1998 | Kochman et al. |
| 5,925,275 A | 7/1999 | Lawson et al. |
| 6,097,009 A | 8/2000 | Cole |
| 6,111,233 A | 8/2000 | Rock et al. |
| 6,218,644 B1 * | 4/2001 | Zorn et al. .................. 219/211 |
| 6,229,123 B1 | 5/2001 | Kochman et al. |
| 6,268,595 B1 | 7/2001 | Haenel |
| 6,331,695 B1 * | 12/2001 | West .......................... 219/212 |
| 6,389,681 B1 | 5/2002 | Rock et al. |
| 6,483,087 B2 | 11/2002 | Gardner et al. |
| 2004/0045955 A1 | 3/2004 | Rock et al. |

FOREIGN PATENT DOCUMENTS

| | | |
|---|---|---|
| DE | 197 45 889 | 4/1999 |
| EP | 0 571 978 | 1/1993 |
| EP | 1 021 064 | 7/2000 |
| GB | 581 212 | 10/1946 |
| GB | 587 189 | 4/1947 |
| GB | 653 641 | 5/1951 |

* cited by examiner

ELECTRIC HEATING/WARMING FABRIC ARTICLES

CROSS-REFERENCE TO RELATED APPLICATIONS

This application is a continuation-in-part application of U.S. patent application Ser. No. 10/339,083, filed Jan. 9, 2003, which claims benefit from U.S. Application No. 60/386,180, filed Jan. 14, 2002, now abandoned. Each of these applications is expressly incorporated by reference herein.

TECHNICAL FIELD

The invention relates to electrical resistance heating/warming textile articles.

BACKGROUND

Techniques known for augmenting heating/warming capabilities of clothing fabric include adding electric wires to the fabric, typically by incorporating the wires directly into the fabric or by attaching the wires to the fabric, e.g., by sewing. It is also known, e.g., from Gross et al. U.S. Pat. No. 4,021,640, to print an electrical circuit with a resistance heating element on a plastic sheet, such as MYLAR®, and to incorporate strips of the plastic sheet into a fabric article, such as a glove.

SUMMARY

In one aspect, the invention features a method of forming an electric heating/warming fabric article, the method comprising: (a) configuring a conductive sheet-form layer comprising a metallized sheet or a conductive textile into an electrically conductive circuit pattern; and (b) attaching the circuit pattern to one of a first and a second broad surface of a fabric body for producing localized heating of the fabric body upon application of electrical current to the circuit pattern.

Using a sheet-form conductive layer to form the circuit pattern provides a robust, flat, and pliable heating/warming element that can be easily manufactured and readily attached to a textile to form a fabric article. The flexible nature of the conductive layer provides good dexterity when the heating/warming element is used in a glove or other article of clothing in which flexibility is useful. The sheet-form conductive layer can also be readily configured in various circuit patterns and geometries, e.g., to provide differential heating to different areas of an article, as will be discussed further below.

Some implementations of this aspect of the invention may include one or more of the following features. The configuring step includes cutting, for example die-cutting, laser cutting, or cutting using ultra sound. The conductive layer includes a metallized sheet material selected from the group consisting of metallized textiles, metallized plastic sheeting, and metal foils. The configuring step includes subjecting a sheet material to metal coating, plating or deposition. The attaching step includes joining the conductive layer and fabric body with adhesive. The term "adhesive," as used herein, refers to any material that will join the layers, including both liquid adhesives and non-liquid, flowable materials such as hot melt webs (commercially available, e.g., from Bostik Co.).

The method further includes forming an article of clothing including the fabric body. The forming step includes shaping the circuit pattern to conform to the shape of the article of clothing. The article of clothing includes an article selected from the group consisting of gloves, socks, sweaters, jackets, shirts, pants, hats, and footwear.

In some implementations, by varying the effective electricity-conducting volume, e.g., the cross-sectional area, of the heating/warming element in selected regions, the level of heat generation can be controlled. (For heating/warming elements of uniform thickness, e.g., those formed of metal foil, the effective volume is typically adjusted by variation of the width and/or length.) For example, in a heating/warming element of the invention for use in a shoe, the volume of the heating/warming element in the region of the toes may preferably be less than its volume in the heel region, thus creating greater resistivity in the region of the toes and greater heat generation. Similarly, for use in gloves, the effective volume of the heating/warming element in the region of the fingers will preferably be less (for greater resistivity and heat generation) than in the palm region.

The method further includes configuring the circuit pattern to include areas of relatively higher resistivity and areas of relatively lower resistivity to provide predetermined regions of relatively higher and relatively lower localized heating. The predetermined areas of relatively higher and relatively lower resistivity are provided by varying the cross-sectional area of one or more selected regions of the circuit pattern. The predetermined areas of relatively higher and relatively lower resistivity are provided by varying the conductivity of one or more selected regions of the conductive layer. The electric heating/warming article is incorporated into an article of clothing, and the method further includes configuring the circuit pattern to place the areas of relatively higher resistivity adjacent a wearer's extremities when the article of clothing is worn, and/or to place the areas of relatively higher resistivity adjacent regions of the wearer's body where blood flow is close to the skin surface when the article of clothing is worn. This allows more heat to be delivered to the extremities, which are prone to vasorestriction in cold weather.

In some instances, heat can be provided to a user's extremities by providing heat to a region from where a large volume of blood supply flows, for example the wrist. In general, an area of relatively high resistivity can be provided adjacent to a major blood vessel or vessels larger than capillaries that pass sufficiently near the skin surface. Accordingly, heat may be conducted directly from the surface of the skin into the blood flowing through the major blood vessel or vessels toward a body extremity, providing heat to the extremity.

The method may also include interposing a barrier layer between the fabric body and the sheet-form conductive layer, e.g., by attaching an outer surface of the barrier layer to the fabric layer, and attaching an inner surface of the barrier layer to the sheet-form conductive layer. The attaching steps may include joining the layers with adhesive. A barrier is generally used if wind protection is desired.

The method further includes connecting the circuit pattern to a power source, to generate heating/warming. The method further includes incorporating the electric heating/warming fabric article into a home textile article, e.g., a blanket, throw, mattress cover or sleeping bag.

In another aspect, the invention features a heating/warming fabric article, including: (a) a fabric layer having an inner surface and an outer surface, and, (b) attached to the inner surface of the fabric layer, a sheet-form conductive layer including an electrically conductive circuit pattern for producing localized heating of the fabric article upon application of electrical current to the circuit pattern.

Some implementations of this aspect of the invention include one or more of the following features. The fabric layer includes a textile material selected from the group consisting of weft knitted materials, warp knitted materials, woven materials, and nonwoven materials. The fabric layer may have a smooth surface, a raised surface, or a brushed surface. The fabric article is an article of clothing. The fabric article is a blanket. The article of clothing includes an article selected from the group consisting of gloves, socks, sweaters, jackets, shirts, pants, hats, footwear, accessories such as ear muffs and neck warmers, and braces and pads such as medical braces, medical bands, knee pads, back pads, and joint pads.

The circuit pattern includes areas of relatively higher resistivity and areas of relatively lower resistivity to provide predetermined regions of relatively higher localized heating and predetermined regions of relatively lower localized heating. The areas of relatively higher and relatively lower resistivity include regions of relatively lesser and relatively greater cross-sectional area, respectively. The fabric article includes an article of clothing, and the circuit pattern is configured to place the areas of relatively higher resistivity adjacent a wearer's extremities when the article of clothing is worn, and/or to place the areas of relatively higher resistivity adjacent regions of the wearer's body where arteries are close to the skin surface when the article of clothing is worn.

The conductive layer includes a sheet-form material selected from the group consisting of metallized textiles, metallized plastic sheeting, and metal foils. The fabric article further includes adhesive interposed between the metallized layer and fabric body. The fabric article may further include a barrier layer between the fabric layer and sheet-formed metallized layer. The fabric layer, sheet-formed conductive layer, and barrier layer (if present) are joined by adhesive.

The fabric article further includes a temperature sensor for measuring the temperature of a portion of the circuit pattern. The temperature sensor is configured to measure the temperature of a first portion of the circuit pattern, and the first portion of the circuit pattern is configured to have the same resistance as a second portion of the circuit pattern, to allow the temperature of the second portion to be estimated by measuring the temperature of the first portion. For example, a first section can be positioned in the bottom of a glove with resistance similar to the resistance of a second section positioned in the extremities of the glove, for example the finger tips. The fabric article further includes a controller configured to adjust the power supplied to the circuit pattern in response to changes in the measured temperature. For example, the temperature controller can be set to be activated if the temperature of the sensor drops below a predetermined setting.

In a further aspect, the invention features a method of forming an electric heating/warming fabric article, the method including: (a) die-cutting a sheet-form conductive layer to form an electrically conductive circuit pattern wherein a first portion of the conductive layer is relatively narrower to increase localized heating and a second portion of the conductive layer is relatively wider to decrease localized heating; (b) attaching the circuit pattern to an outer surface of a fabric body; (c) incorporating the fabric body into an article of clothing; and (d) connecting a power source to the circuit pattern, thereby producing localized heating of the fabric body upon application of electrical current to the circuit pattern. In step (a), the second portion of the conductive layer may be made sufficiently wide that the second portion does not heat up at all, and functions only as a bus.

The details of one or more embodiments of the invention are set forth in the accompanying drawings and the description below. Other features, objects, and advantages of the invention will be apparent from the description and drawings.

DESCRIPTION OF DRAWINGS

FIG. 12 is a somewhat diagrammatic exploded side edge view of the components forming another embodiment of a heating/warming composite fabric article constructed in accordance with the invention, while

Like reference symbols in the various drawings indicate like elements.

DETAILED DESCRIPTION

This application relates to the disclosure of our prior co-pending patent applications U.S. application Ser. No. 09/298,722, filed Apr. 23, 1999, U.S. application Ser. No.

09/389,761, filed Sep. 9, 1999, U.S. Application No. 60/175, 202, filed Jan. 10, 2000, U.S. Application No. 60/261,544, filed Jan. 12, 2001, U.S. Application No. 60/386,180, filed Jan. 14, 2002, and U.S. patent application Ser. No. 10/339, 083, filed Jan. 9, 2003 the complete disclosure of each of which is incorporated herein by reference.

According to one preferred embodiment of the invention, the heating/warming element 16 consists of die cut conductive sheet material, through which an electric current is conducted for producing local heating. The conductive sheet material may be, for example, a metallized sheet, e.g., a metallized textile or metallized plastic sheeting or a metal foil, or a conductive textile, e.g., a knitted, woven or non-woven material containing conductive fibers or yarns. The heating/warming element may be incorporated, e.g., directly or in the form of a textile laminate, into articles of clothing or footwear, and into home furnishings such as blankets and the like. Electric current, e.g. alternating current, via a power cord and plug, or direct current, via a battery, is then applied through the element to cause generation of heat, due to electric resistance.

Figure 1:
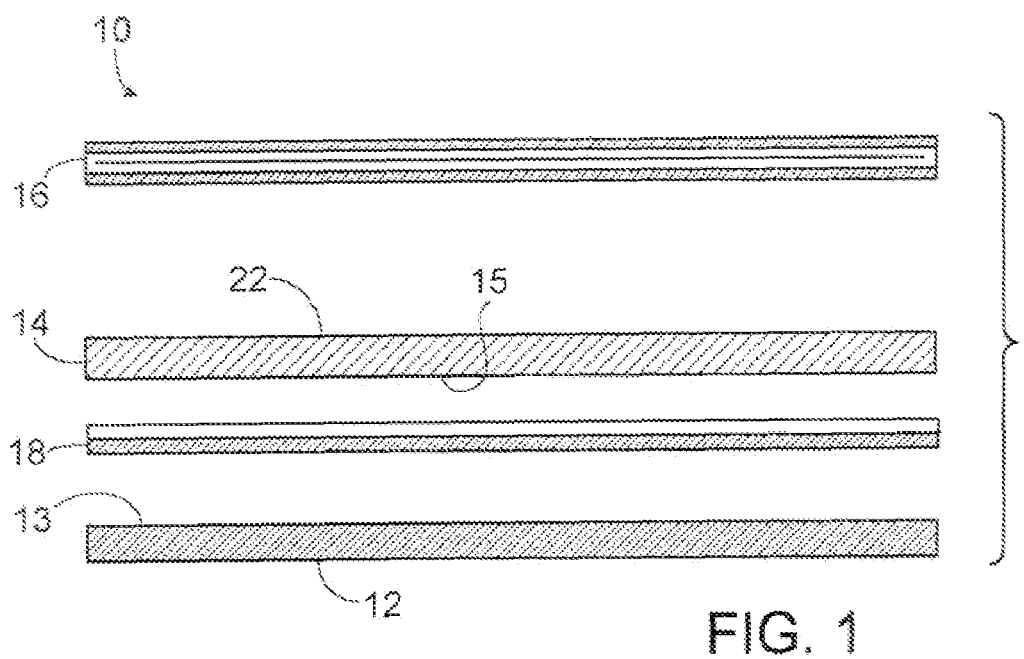
FIGS. 1 and 1A are somewhat diagrammatic exploded side edge views of the components forming the first embodiments of a heating/warming composite fabric article constructed in accordance with the invention.
Figure 2:
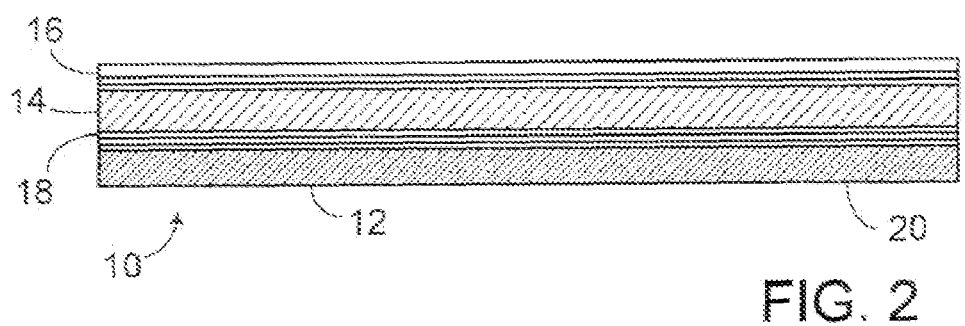
FIG. 2 is a somewhat diagrammatic side edge view of the heating/warming composite fabric article of FIG. 1.

Referring first to FIGS. 1 and 2, in a first embodiment, a windproof, water-resistant, and vapor permeable electric heating/warming composite fabric article 10 constructed in accordance with this invention has three major components. These components include a fabric layer 12, a barrier layer 14 and an electric heating/warming element 16, the fabric layer 12 and barrier layer 14 being joined at opposed fabric inner surface 13 and barrier outer surface 15, respectively, by adhesive 18.

Figure 1A:
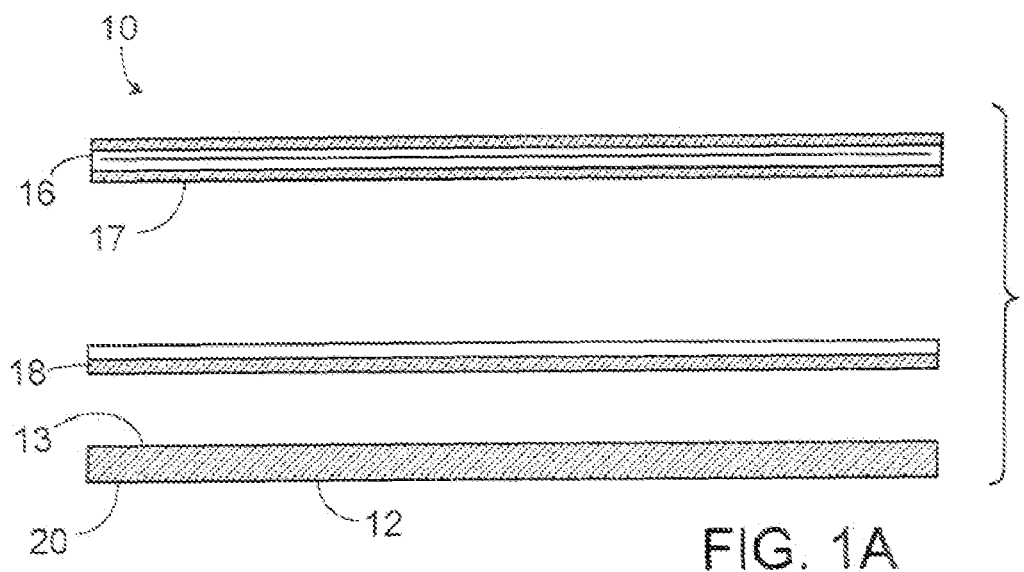

Referring to FIG. 1A, in another embodiment the barrier layer 14 may be omitted. In this case, the electric heating/warming composite fabric article includes a fabric layer 12 and an electric heating/warming element 16. The fabric layer 12 inner surface 13 is joined to the inner surface 17 of the electric heating/warming element 16 by adhesive 18.

In both of the embodiments shown in FIGS. 1 and 1A, the fabric article 10 may further include a second fabric layer (not shown), with the heating/warming element and the barrier layer (if included) being interposed between the two fabric layers.

Referring to FIGS. 1, 1A, and 2, in preferred embodiments, the fabric layer 12 is made in any well known manner, e.g. the fabric layer 12 may be a knitted material, e.g., a plaited circular knitted or reverse plaited circular knitted material, or other circular knitted material (such as double knitted, single jersey knitted, two-end fleece knitted, three-end fleece knitted, terry knitted or double loop knitted material), or warp knitted or weft knitted material, or a woven or non-woven material. In applications where the fabric layer 12 of the fabric article 10 will be directed outwardly, away from the wearer's skin, the material of the fabric layer is preferably hydrophobic, in order to resist penetration of liquids. In other applications, where the fabric layer 12 of the fabric article 10 will be directed inwardly, toward the wearer's skin, the material of the fabric layer is preferably naturally hydrophilic, chemically rendered hydrophilic, or hydrophobic, in order to enhance removal and transport of perspiration away from the skin. The inner surface 13 of fabric layer 12, to which the adhesive 18 is adhered, is preferably flat. The exposed, outer surface 20 of fabric layer 12 may be flat or raised, e.g. by brushing, sanding or napping, and/or may be otherwise provided with decorative and functional features and finishes, e.g. as well known in the art.

Preferably, the barrier layer 14 is formed of a vapor permeable membrane which is nonporous hydrophilic or micro-porous hydrophobic or a combination of both, e.g. in layers, as appropriate to the nature of the intended use, or as otherwise desired. In certain embodiments, it may also be preferred that the material of the barrier layer 14 be soft and stretchable. The barrier layer is constructed and/or formulated to resist air and water droplets from passing through the composite fabric article 10 while being permeable to water vapor. In applications where it is desired that the fabric article 10 is stretchable, the fabric layer 12 may typically be a knitted material, and a preferred material for barrier layer 14 is poly urethane, e.g. as available from UCB Chemical Corp. of Drogenbos, Belgium, either micro-porous hydrophobic (preferred for use where the barrier layer 14 is directed outward) or nonporous hydrophilic (preferred for use where the barrier layer 14 is directed inward). Alternatively, in situations where relatively less stretch is required, e.g. in footwear, the fabric layer 12 may be a warp knitted material, and a preferred material for barrier layer 14 is poly tetrafluoroethylene (PTFE), e.g., as available from Tetratec, of Feasterville, Pa.

Figure 3:
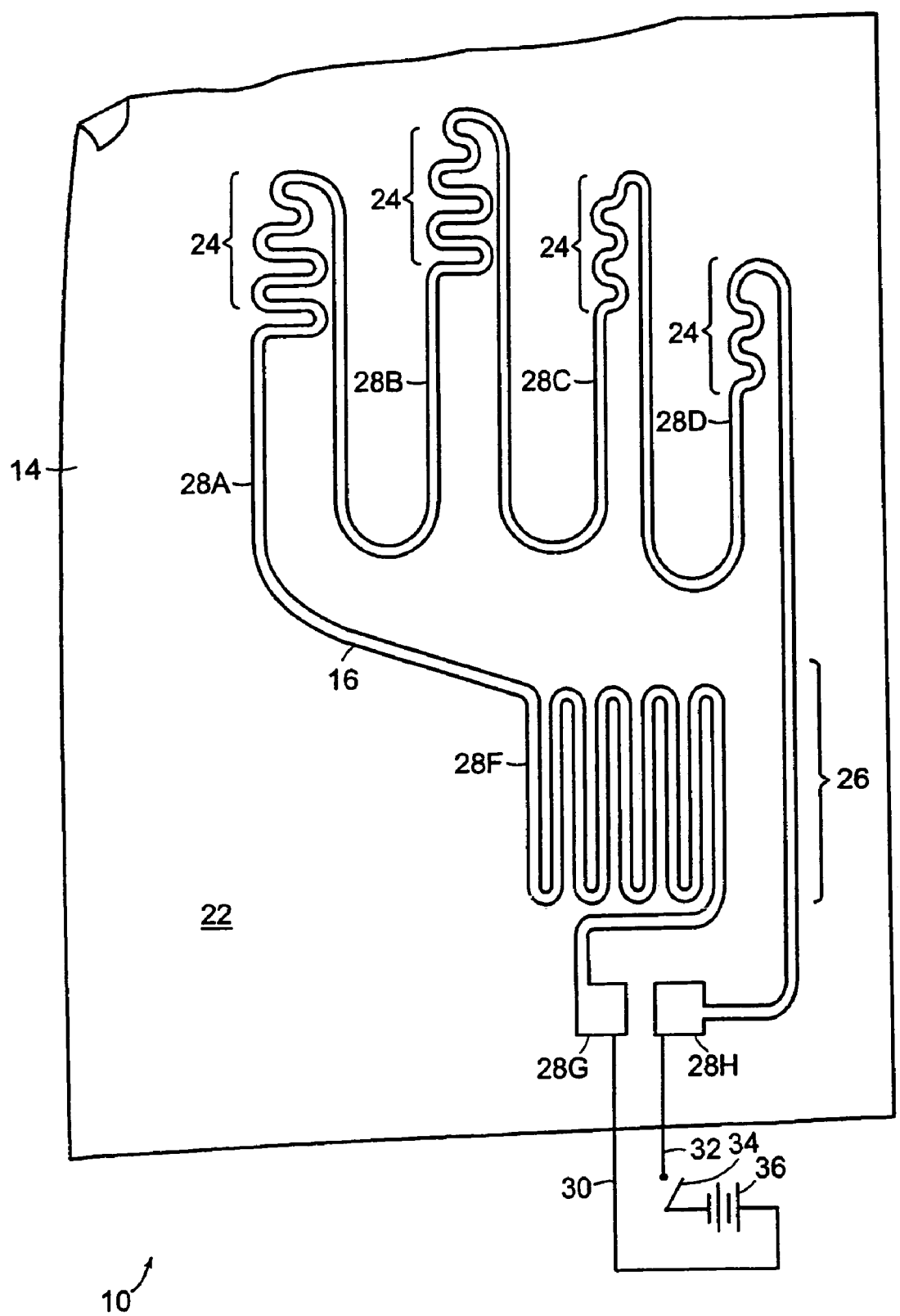
FIGS. 3, 4 and 5 are somewhat diagrammatic front plan views of the inner surfaces of heating/warming composite fabric articles of FIGS. 1 and 2, with electric heating/warming elements affixed thereupon, e.g., for a glove (FIG. 3), for an article of footwear (FIG. 4), and for a garment such as a shirt or jacket (FIG. 5)

The barrier layer 14 is joined to the inner surface 13 of fabric layer 12 by adhesive 18, typically applied in spots, lines or other discrete regions, or by attachment, lamination or other suitable manner of combining. A similar composite fabric (but having an additional internal fabric layer) is described in commonly assigned Lumb et al. U.S. Pat. No. 5,364,678, the entire disclosure of which is incorporated herein by reference. Referring also to FIG. 3, electric heating/warming element 16 is disposed upon the outer surface 22 of barrier layer 14.

In one embodiment, the electric heating/warming element 16 is formed of metallized textile or plastic sheeting or metal foil. Suitable metallized textiles are available, e.g., from Schlegel Systems Inc. of Rochester, N.Y. The textile may be metallized by any suitable technique, e.g., by metal coating, plating, or deposition, using chemical, electrical or mechanical techniques. The metal coating or deposit is made of a conductive material that provides a very low resistance, typically less than about 500 ohms per square. Examples of suitable conductive materials include silver, copper, nickel, nickel-chrome, and combinations of these metals. The metallized textile or plastic sheeting or metal foil can be produced in any desired electrically continuous (in whole or in part) circuit pattern or produced in sheets and then die cut into the desired pattern. The element (or its parts) is then attached or inserted, e.g., alone or laminated to or between one or two layers of suitable non-conductive material, to, or into, the fabric layer 12, to form a textile product. For a textile article in the form of a blanket, formation of the electric heating/warming element as a die cut stamping allow the buses to be formed integrally with the heating elements. The heating elements may be spaced asymmetrically so that selected regions get preferentially warmer than other regions, or, as described in more detail below, by providing selected heating elements that are relatively more narrow than other heating elements, greater resistivity, with resultant generation of more heat, can be provided to selected regions.

Alternatively, the heating/warming element may be formed of a conductive textile, e.g., a textile that includes conductive fibers and/or yarns. Suitable conductive fibers and yarns include, for example, carbon and polyaniline.

The predetermined pattern of the heating/warming element 16 may be custom designed for the particular purpose for which the composite fabric article 10 of the invention is to be used. For example, the pattern of the heating/warming element 16 of the composite fabric article 10 of FIG. 3 is designed for use in making a glove. For this purpose, the electric heating/warming element 16 forms a pattern having four elongated branches 28A, 28B, 28C, 28D (corresponding to fingers of a glove) and one or more sections 28F (corresponding to the palm or back of the body of a glove).

The heating/warming element 16 is formed as a continuous circuit, terminating at each end in a contact pad 28G, 28H, respectively. The contact pads preferably are disposed adjacent to each other in a region convenient for connection to a source of power, e.g. for a glove, as shown, in a region to form the wrist of the glove. Still referring to FIG. 3, the heating/warming element 16 is connected, by wire conductors 30, 32 extending from contact pads 28G, 28H, respectively, in a circuit including a switch 34 and a power supply, e.g., a battery pack 36. When switch 34 is closed, the heating/warming element 16 is activated to generate heat/warmth.

The pattern features of the heating/warming element 16 shown in FIG. 3 are sized and shaped to conform to the regions of the resulting fabric article, i.e., the glove, so that the composite fabric can readily be cut to form one side of a glove. Patterns for use in other types and sizes of garments and fabric articles, e.g. such as socks, sweaters, jackets, shirts, pants, hats, gloves, footwear (e.g. shoes and boots) and so on, can be generated in a similar manner, e.g., as will be discussed below with reference to FIGS. 4–6.

Figure 4:
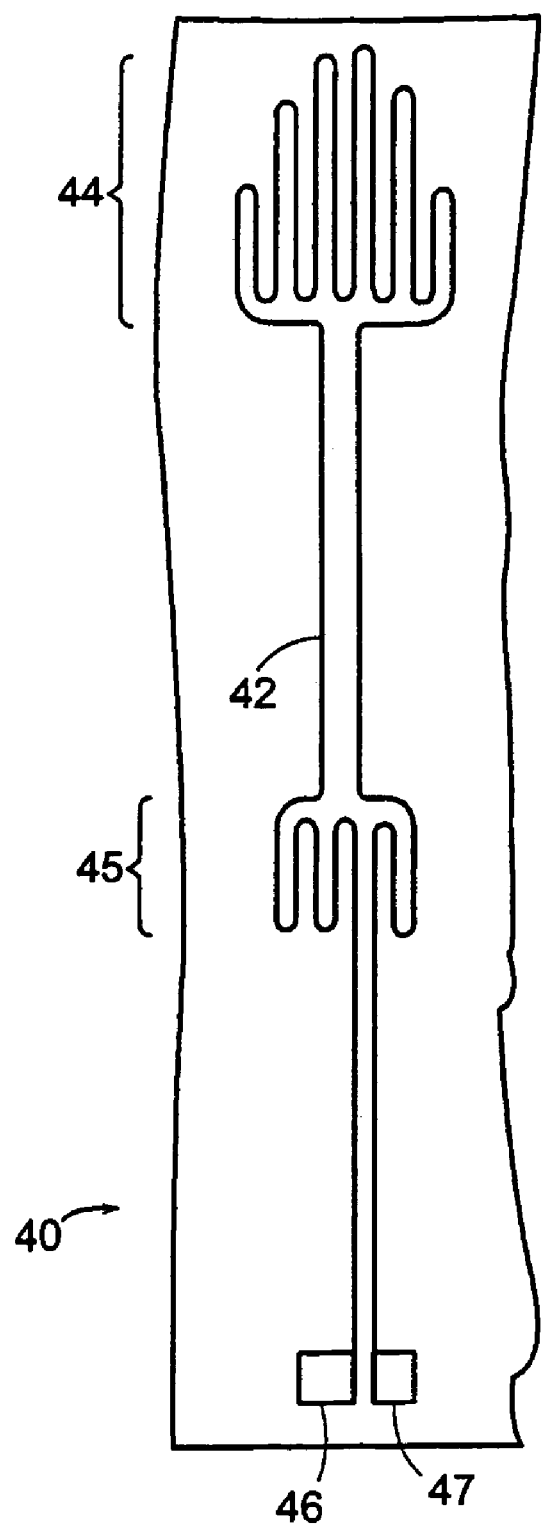

Referring to FIG. 4, a composite fabric article 40 of the invention has a heating/warming element 42 sized and shaped to conform to the regions of the selected resulting fabric article, i.e., in this embodiment, a boot, to be heated/warmed so that the composite fabric can readily be cut to be formed and/or incorporated into a boot liner. In particular, the heating/warming element 42 has heating/warming regions 44, 45, with sections of relatively reduced cross-sectional area for increased resistivity and heat generation, corresponding to the toe/ball and heel surfaces, respectively, of a wearer's foot. The heating/warming element 42, which forms a circuit, terminates at each end in a contact pad 46, 47, respectively. The contacts pads are disposed adjacent to each other in a region convenient for connection to a source of power, e.g., as shown, in a region to extend into or above the ankle collar of the boot.

Figure 5:
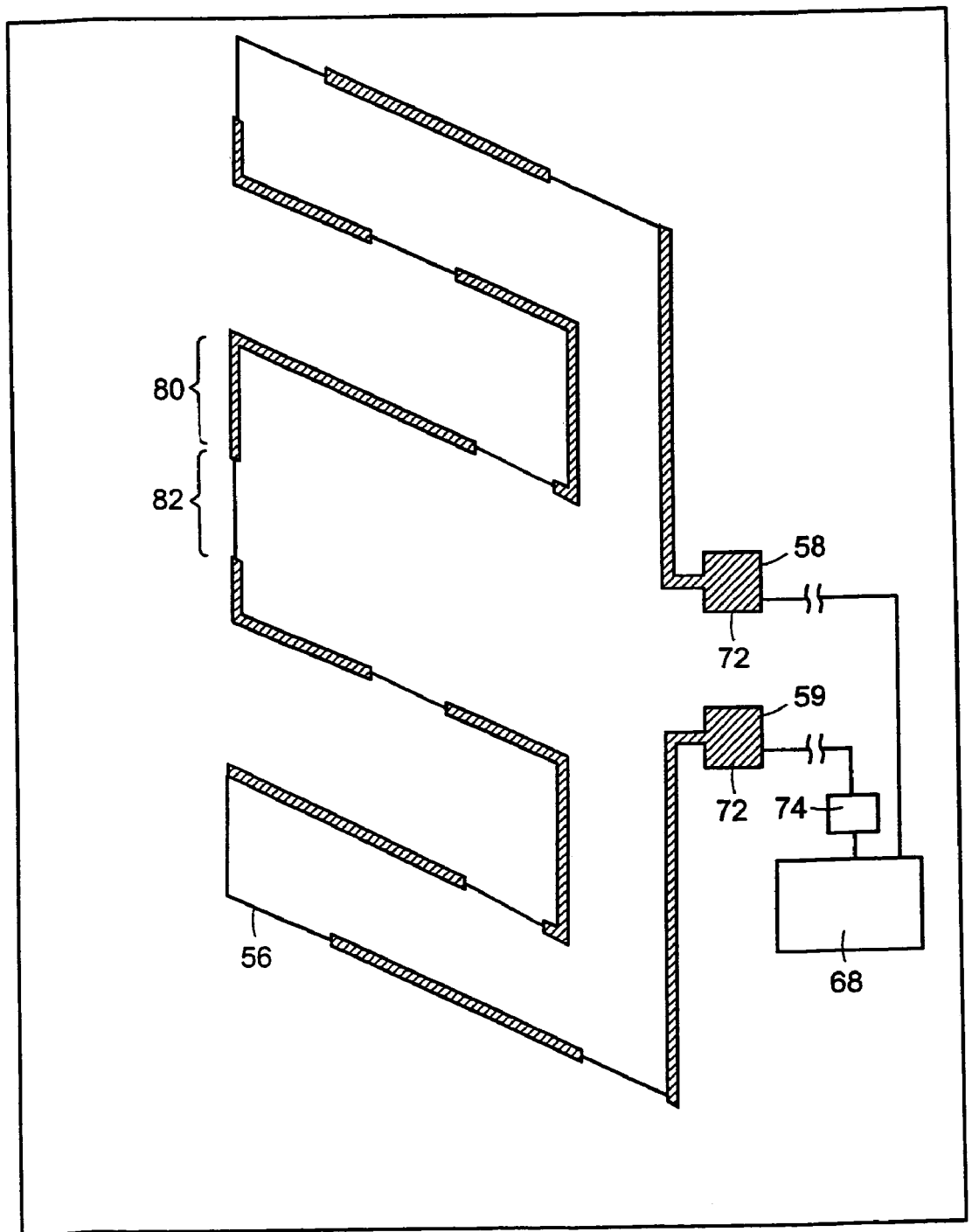

Referring to FIG. 5, a composite fabric article 50 of the invention has a heating/warming element 56 sized and shaped to conform to the regions of the selected resulting fabric article, i.e., in this embodiment, the opposite chest surfaces of a garment such as a shirt or a jacket 60 (FIG. 6), to be heated/warmed. The heating/warming element 56 terminates at each end in a contact pad 58, 59, respectively, the pads being disposed adjacent to each other in a region convenient for connection to a source of power, as discussed below.

Figure 6:
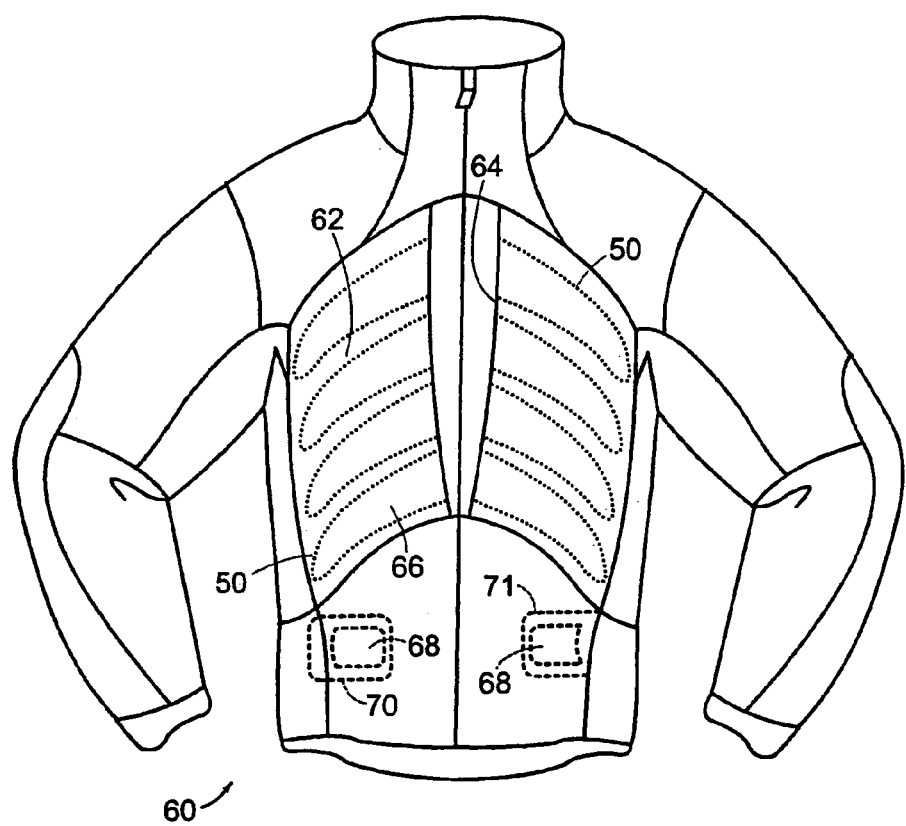
FIG. 6 is a somewhat diagrammatic front view of a garment, i.e., a jacket, incorporating the heating/warming composite fabric article of FIG. 5.

Referring also to FIG. 6, a pair of fabric articles 50 is shown incorporated into jacket 60. A battery pack 68 for powering each of the heating/warming composite fabric articles 50 is contained in the associated zippered pockets 70, 71. The battery pack 68, e.g. as available from Polaroid Corporation, of Cambridge, Mass., is preferably removably connected to the contact pads 58, 59 of heating/warming element 56 by releasable fastening elements 72, e.g. clips, snaps or other secure but releasable fastening elements. (The fastening elements may provide the electrical connection of the battery pack to the circuit, or, alternatively, may maintain the battery pack in position for contact of the battery pack with separate connectors.) This arrangement permits the battery pack 68 to be removed, e.g., whenever the fabric article 50 is to be washed, or for replacement.

The heating/warming circuit 56 may also include an oscillator chip 74 or other timing or cycling device for cycling application of electrical power from the battery pack 68 to the heating/warming element 56, e.g., to extend battery pack life. For example, a timing cycle of three minutes "on" followed by one minute "off" is considered suitable for an electric heating/warming composite fabric article 50 incorporated as a chest panel of the heating/warm jacket 60 suited for outdoors use.

In one preferred embodiment, a composite fabric article 10 of the invention is formed by first combining the fabric layer 12 and barrier layer 14 with adhesive 18 disposed therebetween. An electric heating/warming element 16 is then affixed upon the surface 22 of the barrier layer 14. The resulting composite fabric article 10 is cut to shape, and otherwise processed using standard clothing procedures, for incorporation, e.g., into an article of clothing or the like. Alternatively, the heating/warming element 16 may be affixed upon the surface 22 of the barrier layer 14, before the barrier layer 14 and the fabric layer 12 are secured together.

Figure 7:
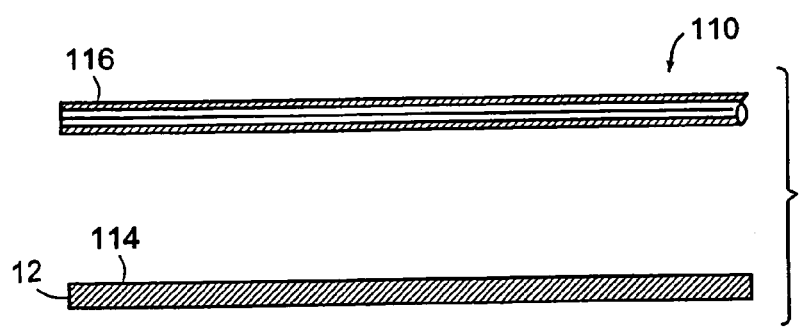
FIG. 7 is a somewhat diagrammatic exploded side edge view of the components forming another embodiment of a heating/warming composite fabric article constructed in accordance with the invention.
Figure 8:
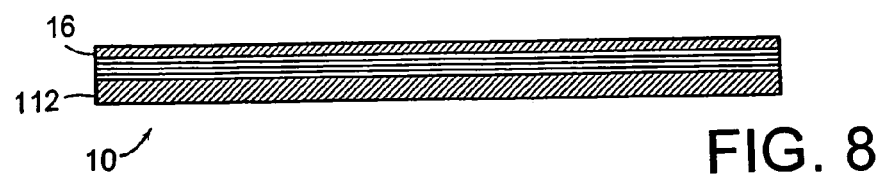
FIG. 8 is a somewhat diagrammatic side edge view of the heating/warming composite fabric article of FIG. 7.

Referring next to FIGS. 7 and 8, in another embodiment of the invention, an electric heating/warming composite fabric article 110 consists of a fabric layer 112 having an inner surface 114 upon which an electric heating/warming element 116 is disposed.

In embodiments of the invention where the heating/warming element 116 is affixed directly to the fabric layer 112, the composite fabric article 110 may be employed without a barrier layer. Alternatively, a pair of fabric articles 110 may be incorporated into a garment, e.g. a jacket 60, as shown in FIG. 6, where the outer coverings 62, 64 of the opposite chest surfaces of the jacket may be a shell material selected to provide a barrier layer overlaying the heating/warming composite fabric articles 110 incorporated into the jacket.

The relative amounts of heat/warmth generated by a region of an electrical heating/warming element in a composite heating/warming fabric article of the invention can be controlled, e.g., by varying the width and/or by varying the length and/or the thickness of a circuit element or segment, and/or by varying the conductivity/resistivity of the material forming a segment of the circuit element.

For example, referring to FIG. 5, a heating/warming element 56 formed of material of uniform conductivity and constant thickness has regions 80 and 82 of contrasting width, and, therefore, contrasting cross sectional area. As a result, in region 80 of relatively greater width, there is more conductivity, i.e. less resistance to current flow, and thus less generation of heat/warmth. Similarly, in region 82 of relatively lesser width, there is less conductivity, i.e. more resistance to current flow, and thus relatively greater generation of heat/warmth. As a result, a composite heating/warming fabric article 50 of the invention can be designed with a circuit element 56 that delivers relatively greater amounts of heat/warmth to selected regions of the wearer's body.

Figure 9:
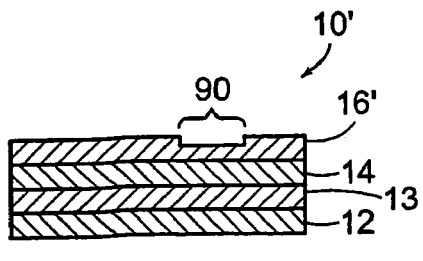
FIG. 9 is a somewhat diagrammatic side edge view of another embodiment of a heating/warming composite fabric article constructed in accordance with the invention.
Figure 10:
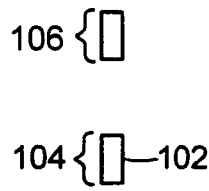
FIGS. 10 and 11 are sequential, somewhat diagrammatic front plan views of the inner surface of a heating/warming composite fabric article during construction in accordance with another embodiment the invention.

Alternatively, this effect may be obtained by applying a thinner layer of material, i.e., a region of relatively lesser cross sectional area. For example, referring to FIG. 9, a composite heating/warming fabric article 10' of the invention has a heating/warming element 16' having a region 90 of relatively lesser thickness (compared to adjacent regions).

Alternatively, or in addition, a heating/warming element of constant dimension but with regions generating relatively different levels of heat/warmth may be formed by sequentially applying circuit regions using materials of inherently different conductivity. For example, referring first to FIG.

Figure 11:
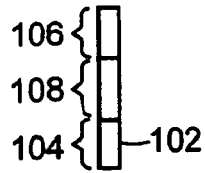

10, showing a composite heating/warming fabric article 100 of the invention, a heating/warming element 102 is formed by affixing regions 104, 106 of a material of relatively greater conductivity, and thereafter, referring to FIG. 11, affixing region 108 of a material of relatively lower conductivity, region 108 interconnecting regions 104, 106.

These and other methods for adjusting the conductivity of electrical circuit regions may be employed alone, or in any desired combination.

The conductivity of various regions of the electrical circuit may be adjusted to suit the requirements of a particular application and thereby enhance wearer comfort. For example, in the case of gloves or footwear, heating the extremities (fingers and toes) is important to providing comfort, and generally the fingers and toes, especially at their tips, require more heating than the rest of the hands and feet. Thus, it is may be desirable to generate more heat in these specific areas, which may be accomplished in any of the manners discussed above.

Figure 15:
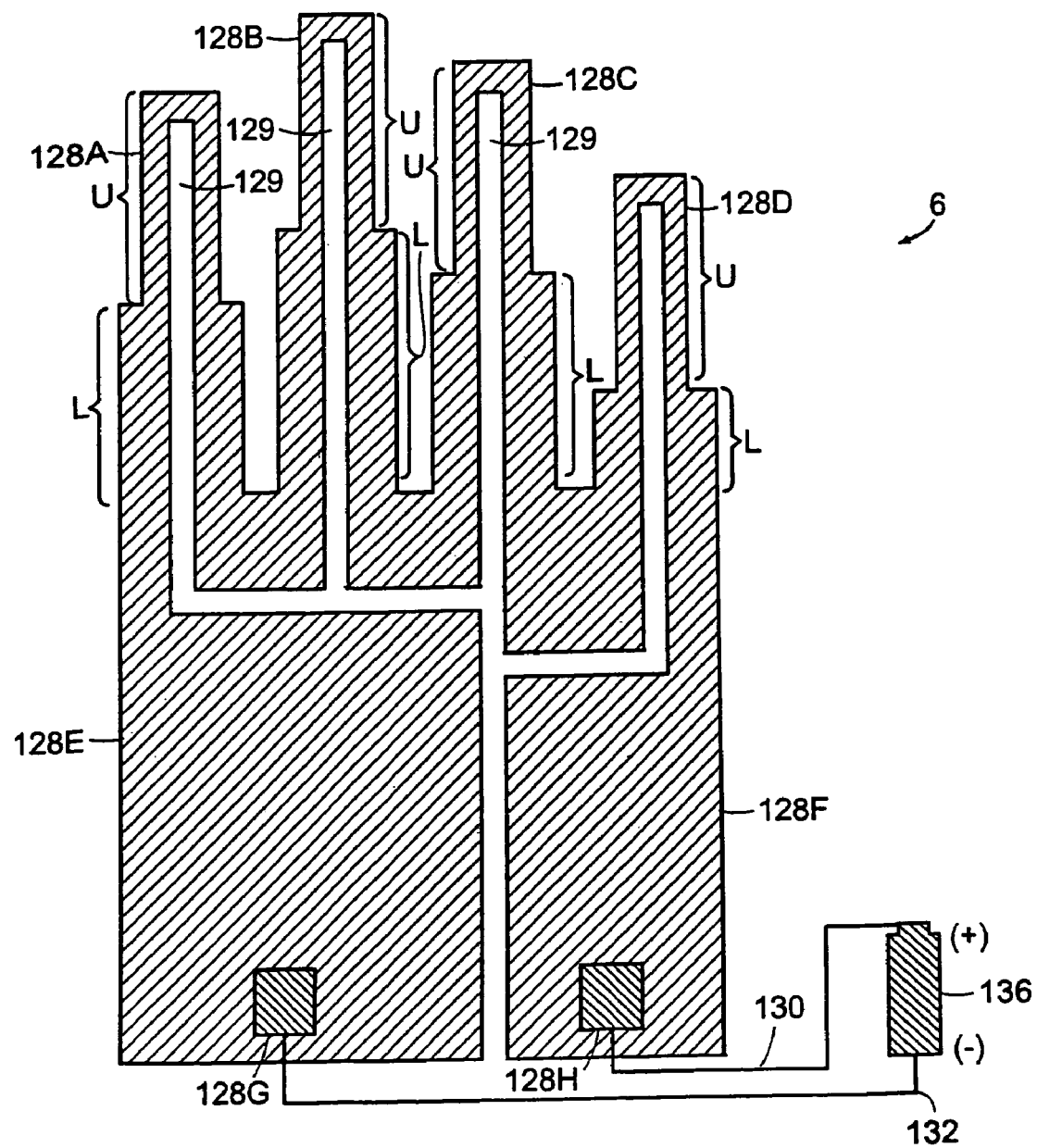
FIGS. 15–17 are somewhat diagrammatic front plan views of an electric heating/warming element for use in a glove.
Figure 16:
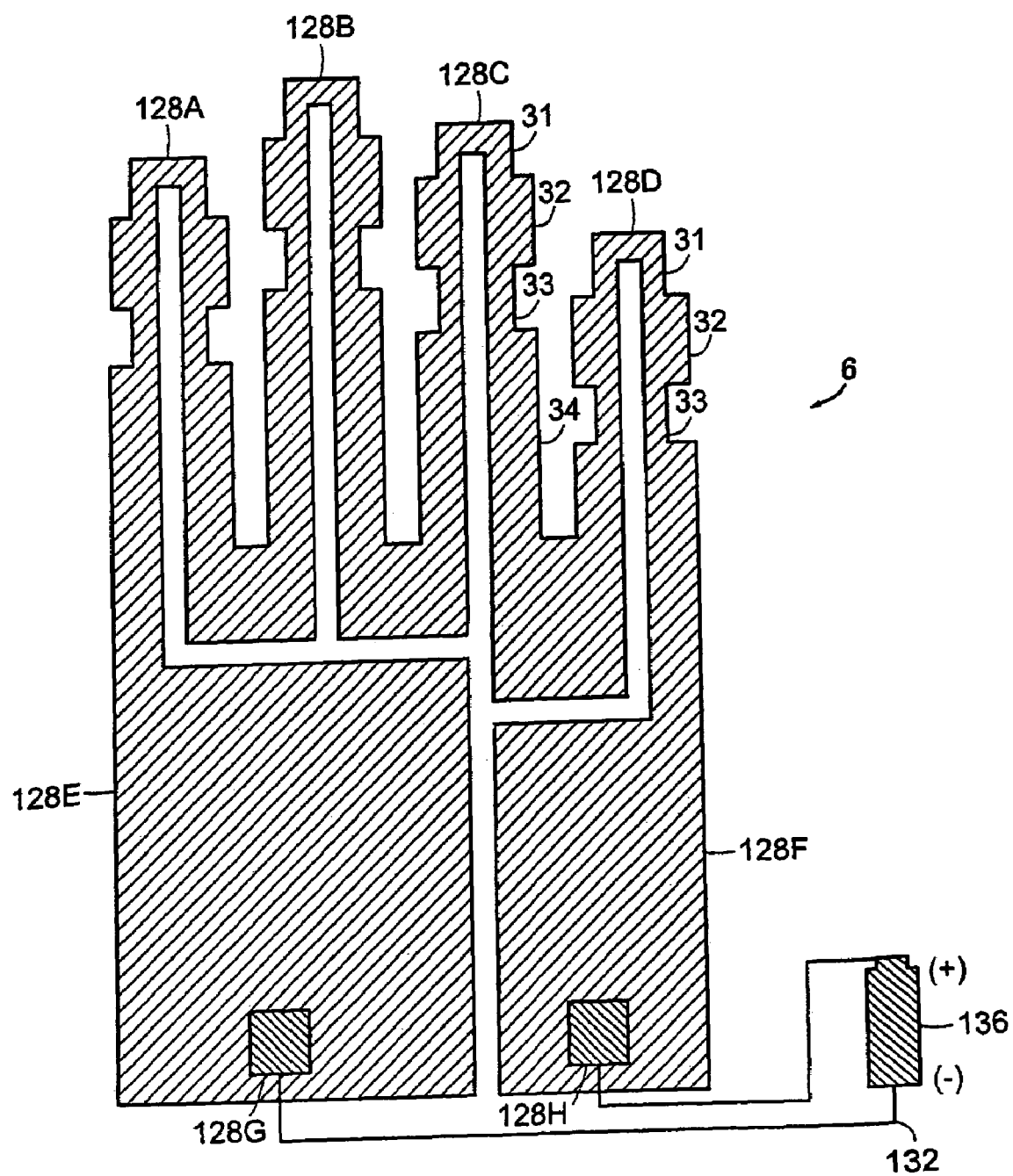

Preferred heating elements for use in gloves are shown in FIGS. 15 and 16. In both of these embodiments, the electric heating/warming element 116 forms a pattern having four elongated branches 128A, 128B, 128C, 128D (corresponding to fingers of a glove) and sections 128E and 128F (corresponding to the palm or back of the body of a glove). A region 129 is cut out, or is not metallized, to reduce the effective area of the conductive material. The presence of region 129 increases the resistivity of the branches 128A–128D, while not significantly affecting the conductivity of the palm sections 128E and 128F. As a result, more heat will be generated in the branches 128A–128D than in the palm sections.

Additionally, within the branches 128A–128D there are regions of different width. For example, in the embodiment shown in FIG. 15, the branches 128A–128D include upper regions U, generally corresponding to the portion of the wearer's fingers from the first knuckle to the tip, and lower portions L, generally corresponding to the portion of the wearer's fingers from the first knuckle to the intersection of the finger with the palm. The upper regions U are narrower than the lower regions L, and thus have a greater resistivity and as a result generate more heat at the wearer's fingertips.

When the pattern shown in FIG. 15 is powered by 3.0 volts direct current source with an element having a resistance of 4.8 Ohms, the temperature generated in upper portions U is about 101 degrees Fahrenheit while the temperature generated in lower portions L is about 80 degrees Fahrenheit. This provides greater heat generation in the fingers, and particularly at the tips of the fingers, providing more comfort for the user while conserving battery power.

Similarly, in the embodiment shown in FIG. 16, the width of the branches 128A–128D is further varied, to provide narrow areas 31 and 33, generally corresponding, respectively, to the tips and first knuckles of a wearer, and wide areas 32 and 34, generally corresponding to the areas between the knuckles of the wearer. In this example when the element is powered by a 3.0 volts direct current source with the element having a resistance of 4.8 Ohms, the temperature generated at narrow areas 31 and 33 is about 101 degrees Fahrenheit, while the temperature generated at wide areas 32 and 34 is about 80 degrees Fahrenheit. The section next to the terminals and in the palm area will have very low resistance and thus will generate very little, if any, heat. Thus, the narrow areas 31 and 33 provide high heat generation at the fingertips and close to the arteries (at the first knuckle). Providing heat generation at regions close to arteries helps to warm the blood and improve circulation. As a result, the user's fingers are kept warm without overheating the rest of the user's hand, while also conserving battery power.

In some instances, heat can be provided to a user's extremities by providing heat to a region from where a large volume of blood supply flows. For example, heat can be provided through a user's skin and into the user's bloodstream at a vascular surface location defined as an area where a major blood vessel or vessels larger than capillaries pass sufficiently near the skin surface that heat may be conducted directly from the surface of the skin into the blood flowing through the major blood vessel or vessels toward a body extremity. Thus, the heated blood supply is then circulated to the user's extremities, resulting in warmer extremities.

Figure 17:
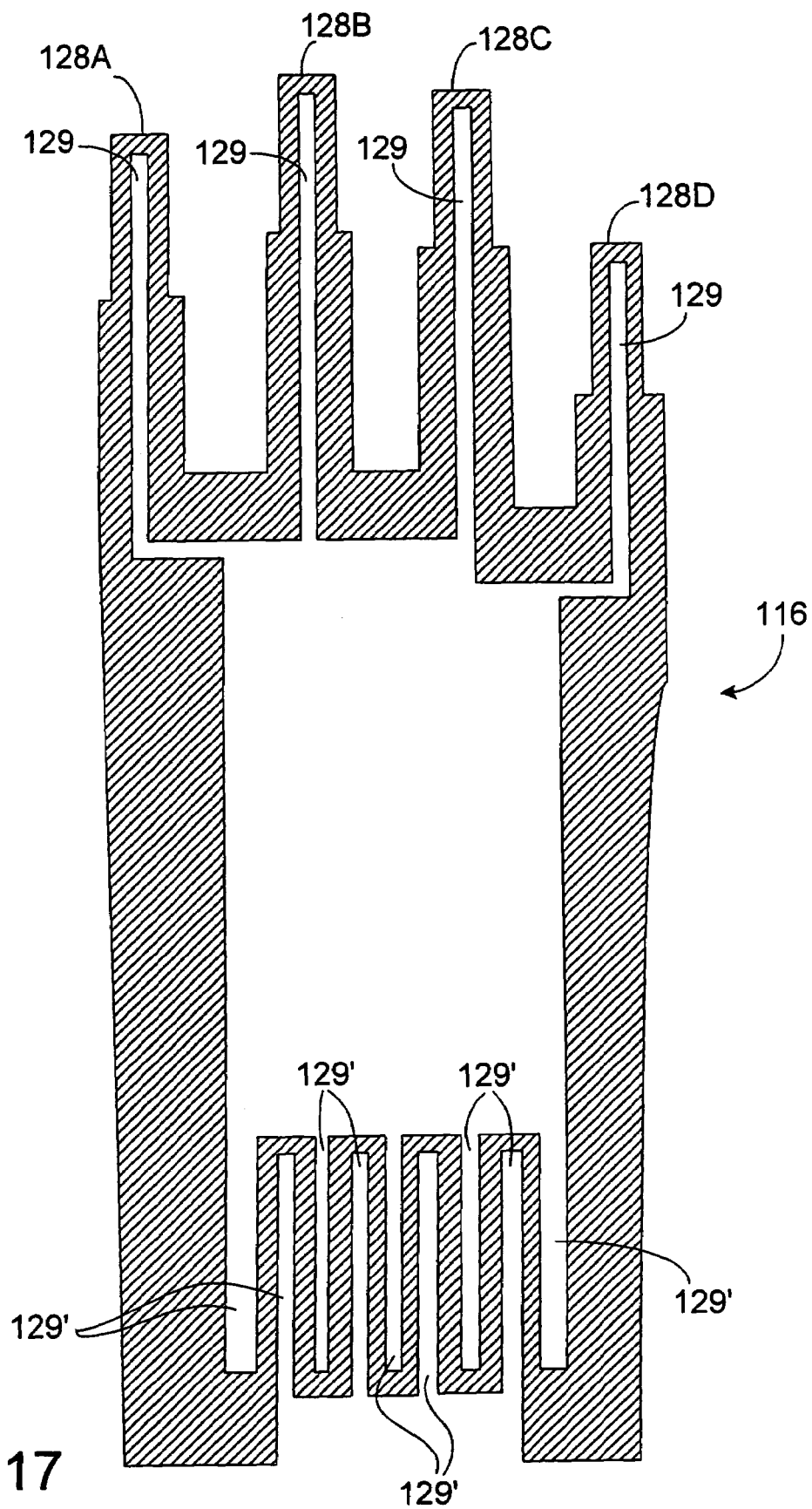

Referring to FIG. 17, the electric heating/warming element 116 forms a pattern having four elongated branches 128A, 128B, 128C, 128D (corresponding to fingers of a glove) placed in a manner similar to that depicted in FIG. 15. As discussed above, the presence of region 129 in the elongated branches increases the resistivity of the fabric article in the elongated branches. Similarly to region 129, a region 129', is not metallized, which reduces the effective area of the conductive material, and increases the resistivity in the corresponding portion of the fabric article. Region 129' is positioned to cover the wrist of the user, where a substantial blood supply flows towards the elongated branches through major blood vessels, so the blood is heated as it passes through the wrist and towards the user's fingers. Accordingly, blood is heated both at the writes, as it flows to the fingers and fingertips, and directly at the fingers and fingertips.

Figure 13:
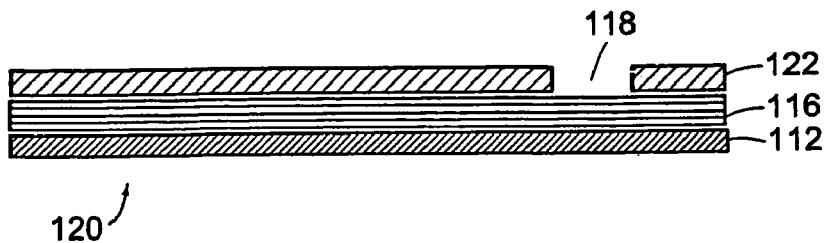
FIGS. 13 and 14 are somewhat diagrammatic side edge views of alternate embodiments of the heating/warming composite fabric article of FIG. 12.
Figure 14:
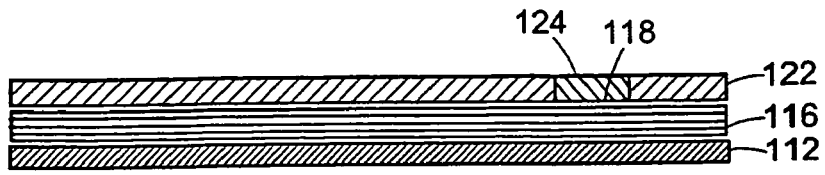

In the embodiments shown in FIGS. 15, 16, and 17 power is delivered to the circuit in the same manner as discussed above with reference to FIG. 3. That is, the heating/warming element 16 is formed as a continuous circuit, terminating at each end in a contact pad 128G, 128H, respectively, for connection to a source of power, e.g., a battery pack 136, by wire connectors 130, 132. In yet another embodiment of the invention, the electric heating/warming composite fabric article 110 described above with reference to FIGS. 5 and 6 may be further processed. For example, referring now to FIGS. 12, 13 and 14, in an electric heating/warming composite fabric article 120, a barrier layer 122, e.g. as described above, is attached adjacent to the side of the inner surface 114 of the fabric layer, overlying at least a portion of the heating/warming element 116, using adhesive, also as described above. Preferably, contact pads 118 (only one is shown) of heating/warming element 116 are left exposed for connection to a source of power (FIG. 13), or electrical connectors 124 (only one is shown) are provided for connecting the contact pads and power source through the barrier layer 122 (FIG. 14).

In all cases described above, the heating/warming element is supported by a fabric layer, whether or not a barrier layer is provided. The fabric layer may be naturally hydrophilic, chemically rendered hydrophilic, or hydrophobic. In some preferred embodiments, a barrier layer is provided at least adjacent to the inner surface of the fabric layer, i.e., attached to the fabric layer (with or without intervening materials) or spaced from attachment to or upon the fabric layer, but positioned at the inner surface side of the fabric.

Figure 12:
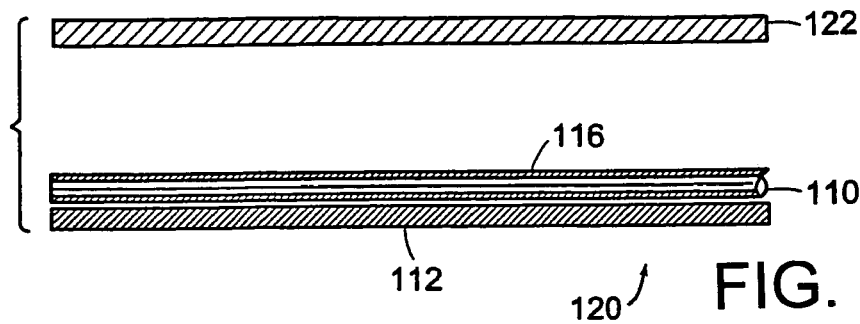

A barrier layer associated with or attached, e.g. by lamination or other techniques, upon the surface of the fabric layer 12 upon which the heating/warming element 16 is affixed (e.g. barrier layers 62, 64; FIG. 6 and barrier layer 122; FIGS. 12–14, respectively) serves also to protect the circuit against the effects of abrasion that might otherwise deteriorate the quality or continuity of the electrical heating circuit. The barrier layer would also serve to resist short-circuiting in the event that condensate forms on the fabric layer inner surface. The barrier layer may be formed of any suitable, protective material. It will preferably be micro porous hydrophobic or nonporous hydrophilic if it is a complete layer. Where a complete layer is not desired or employed, the barrier layer may be applied exclusively to the printed circuit itself, in which case, it will preferably be nonporous hydrophobic.

Figure 18:
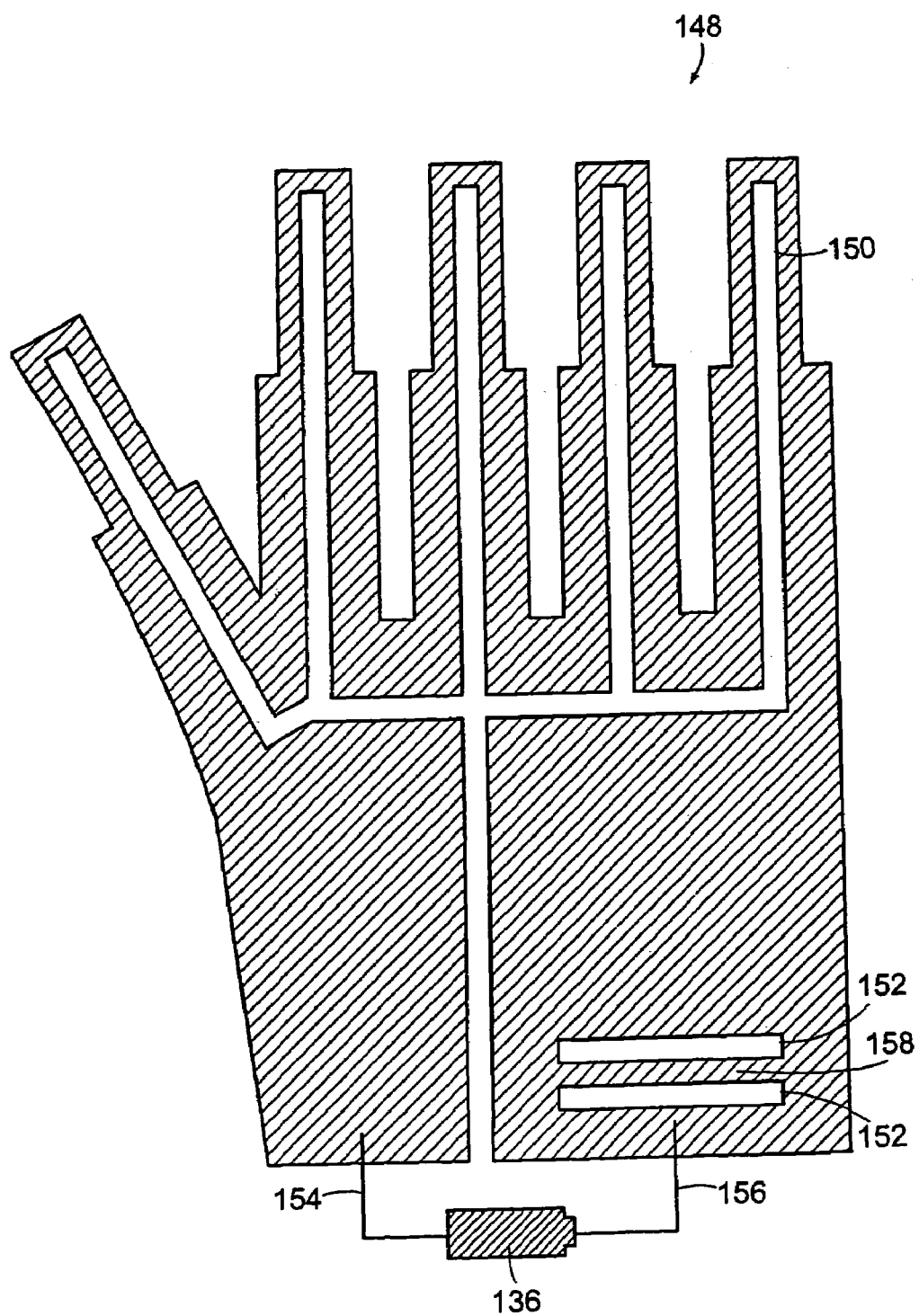
FIG. 18 is a somewhat diagrammatic front plan view of an electric heating/warming element for use in a glove, including a temperature sensing element.

If desired, the temperature of a portion of the heating/warming element can be measured during use. For instance, a sensor can be included to determine the temperature at the fingertip of the glove. The sensor can be placed at the fingertip, with a wire running down the finger. However, this may interfere with dexterity, and thus it may be desirable to simulate the fingertip temperature at another area of the glove and measure the temperature at that area. For example, in the heating/warming element 148 shown in FIG. 18, the temperature at fingertip 150 can be simulated by providing two cut-out areas 152 in the palm region, near the wire conductors 154, 156 that define a rectangular area 158 that is calculated to have the same resistance as the portion of the circuit in the fingertip 150. Thus, the temperature at the fingertip can be estimated remotely by measuring the temperature of the area 158. This temperature data can be used, in conjunction with a controller (not shown), e.g., a voltage regulator, to automatically shut off the battery or deliver less power to the circuit when a maximum temperature is detected, and turn on the battery or increase power delivery when a minimum temperature is detected. Alternatively, or in addition, the temperature can be displayed on a read-out (not shown) mounted on the glove, and a manual control can be provided to allow the wearer to turn the battery on and off or adjust the temperature.

A number of embodiments of the invention have been described. Nevertheless, it will be understood that various modifications may be made without departing from the spirit and scope of the invention.

For example, additional fabric layers may be added to enhance various aesthetic and functional characteristics of the electric heating/warming composite fabric article.

Figure 19:
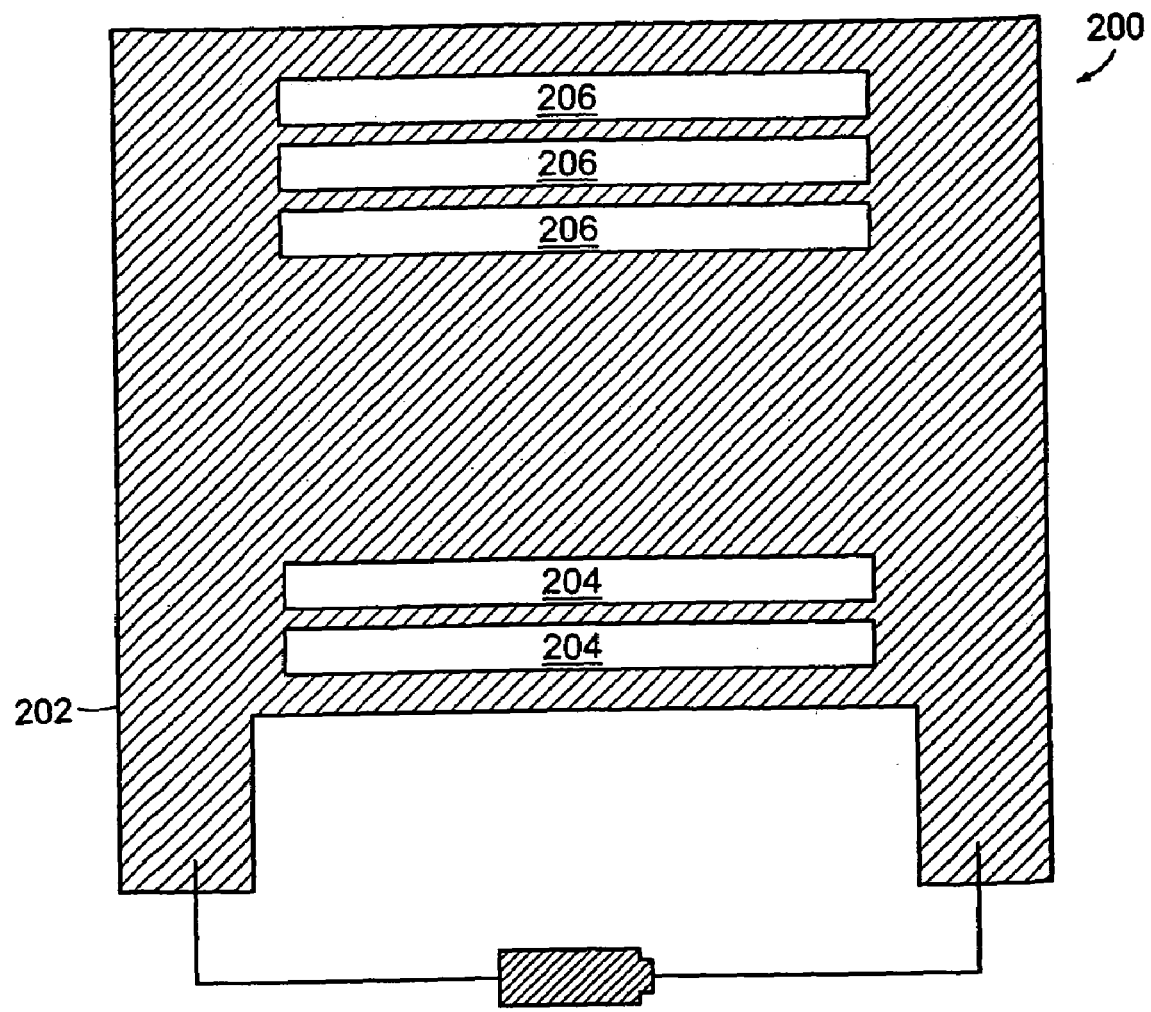
FIG. 19 is a somewhat diagrammatic front plan view of an electric heating/warming element that includes a parallel circuit.

Moreover, while the circuits in the embodiments discussed above have been series circuits, the circuit used in the heating/warming element may be a parallel circuit, e.g., as shown in FIG. 19. In the heating/warming element 200, shown in FIG. 19, the relatively wide areas 202 act as buses, while the cut-out areas 204, 206 provide areas of higher resistivity, as discussed above. The circuit shown in FIG. 19 also illustrates that the circuit need not be symmetrical, e.g., in the circuit shown in FIG. 19 there are three cut-out areas 206 in the upper region of the circuit, but only two cut-out areas 204 in the lower region of the circuit.

Figure 20:
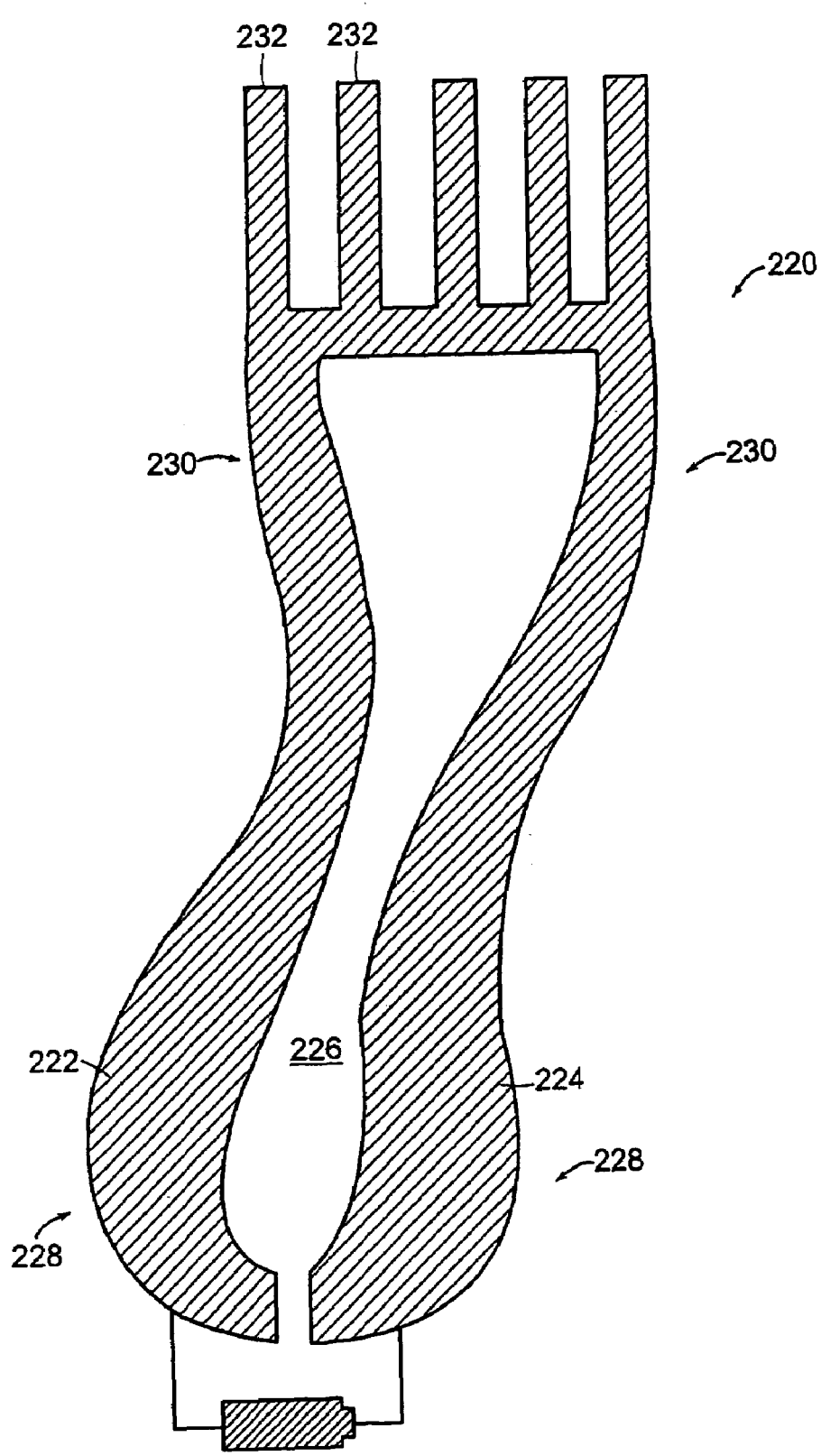
FIG. 20 is a somewhat diagrammatic front plan view of an electric heating/warming element for use in an article of footwear.

Further, while circuits for gloves have been described above, by way of example, the heating/warming element may be used in many different applications. For example, a heating/warming element 220, for use in a sock, shoe, or other article of footwear, is shown in FIG. 20. In the heating/warming element 220, the circuit includes a left hand portion 222 and a right hand portion 224, separated by a cut-out area 226. Cut-out area 226 is shaped to provide relatively wide bus areas 228 in the heel region, and relatively narrower, higher resistivity areas 230 in the forefoot region. The toe portions 232 are narrowest of all, and thus have the highest resistivity, so that the highest temperature will be generated adjacent the wearer's toes.

Accordingly, other embodiments are within the scope of the invention.

For example, although die cut materials are described other means can also be used to cut the conductive fabric. For example the fabric can also be laser cut or cut using ultra sound.

What is claimed is:

1. A heating/warming fabric article comprising:
a fabric layer having an inner surface and an outer surface, and, attached to the inner surface of the fabric layer, heating element in the form a sheet-form conductive layer comprising a metallized sheet or a conductive textile including a bus integrally formed with an electrically conductive circuit pattern for producing localized heating of the fabric article upon application of electrical current to said circuit pattern.

2. The fabric article of claim 1 wherein the fabric layer comprises a textile material selected from the group consisting of well knitted materials, warp knitted materials, woven in materials, and nonwoven materials.

3. The fabric article of claim 1 wherein fabric layer has a smooth surface, a raised surface, or a brushed surface.

4. The fabric article of claim 1 wherein the fabric article comprises an article of clothing.

5. The fabric article of claim 1 wherein the fabric article comprises a blanket, throw, sleeping bag or mattress cover.

6. The fabric article of claim 1 wherein said conductive layer comprises a sheet-form material selected from the group consisting of metallized textiles, metallized plastic sheeting, and metal foils.

7. The fabric article of claim 1 further comprising adhesive interposed between the conductive layer and fabric body.

8. The fabric article of claim 4 wherein the article of clothing comprises an article selected from the group consisting of gloves, socks, sweaters, jackets, shirts, pants, hats, footwear, ear muffs, neck warmers, medical braces, medical bands, knee pads, back pads, and joint pads.

9. The fabric article of claim 4 wherein the circuit pattern comprises areas of relatively higher resistivity and areas of relatively lower resistivity to provide predetermined regions of relatively higher localized heating and predetermined regions of relatively lower localized heating.

10. The fabric article of claim 9, wherein said areas of relatively higher and said areas of relatively lower resistivity comprise regions of relatively lesser and relatively greater cross-sectional area, respectively.

11. The fabric article of claim 9 wherein the circuit pattern is configured to place said areas of relatively higher resistivity adjacent a wearer's extremities when the article of clothing is worn.

12. The fabric article of claim 9 wherein the circuit pattern is configured to place said areas of relatively higher resistivity adjacent regions of the wearer's body where arteries are close to the skin surface when the article of clothing is worn.

13. The fabric article of claim 9 wherein the electric heating/warming article is incorporated into the article of clothing, and the circuit pattern is configured to place said areas of relatively higher resistivity adjacent regions of the wearer's body where blood flows through a major blood vessel or artery.

14. The fabric article of claim 4, further comprising a barrier layer between the fabric layer and sheet-formed conductive layer.

15. The fabric article of claim 13 wherein the barrier layer, fabric layer, and sheet-formed conductive layer are joined by adhesive.

16. The fabric article of claim 1 wherein said circuit pattern comprises a series circuit.

17. The fabric article of claim 1 wherein said circuit pattern comprises a series circuit.

18. The fabric article of claim 1 wherein said circuit pattern is asymmetrical.

19. The fabric article of claim 1 further comprising a temperature sensor for measuring the temperature of a portion of the circuit pattern.

20. The fabric article of claim 19 wherein said temperature sensor is configured to measure the temperature of a first portion of the circuit pattern, and the first portion of the circuit pattern is configured to have the same resistance as a second portion of the circuit pattern to allow the temperature of the second portion to be estimated by measuring the temperature of the first portion.

21. The fabric article of claim 19 further comprising a controller configured to adjust the power supplied to the circuit pattern in response to changes in the measured temperature.

22. A heating/warming fabric article of clothing, comprising:
a fabric layer having an inner surface and an outer surface, and,
attached to the inner surface of the fabric layer, a heating element in the form a sheet-form conductive layer comprising a metallized sheet or a conductive textile including a bus integrally formed with an electrically conductive circuit pattern for producing localized heating of the fabric article upon application of electrical current to said circuit pattern, wherein the circuit pattern is configured to place an area of relatively higher resistivity adjacent regions of the wearer's body where blood flows through a major blood vessel or artery.

23. The fabric article of claim 13 wherein the circuit pattern is configured to place an area of said relatively higher resistivity over the user's wrist.

24. The fabric article of claim 13 wherein the circuit pattern is configured to place an area of said relatively higher resistivity over the user's throat.

* * * * *

UNITED STATES PATENT AND TRADEMARK OFFICE
CERTIFICATE OF CORRECTION

| | | |
|---|---|---|
| PATENT NO. | : 7,202,443 B2 | Page 1 of 1 |
| APPLICATION NO. | : 10/927665 | |
| DATED | : April 10, 2007 | |
| INVENTOR(S) | : Moshe Rock and Vikram Sharma | |

It is certified that error appears in the above-identified patent and that said Letters Patent is hereby corrected as shown below:

Column 13, line 7 please replace "series" with -- parallel --.

Signed and Sealed this

Nineteenth Day of June, 2007

JON W. DUDAS
*Director of the United States Patent and Trademark Office*